United States Patent
Rutten et al.

(10) Patent No.: US 12,426,737 B2
(45) Date of Patent: Sep. 30, 2025

(54) COFFEE OR MILK MACHINE AND METHOD OF OPERATING SUCH A MACHINE

(71) Applicant: Bravilor Bonamat B.V., Heerhugowaard (NL)

(72) Inventors: Mathias Anthonius Franciscus Rutten, Heerhugowaard (NL); Antonius Johannes Spijker, Heerhugowaard (NL)

(73) Assignee: BRAVILOR BONAMAT B.V., Heerhugowaard (NL)

( * ) Notice: Subject to any disclaimer, the term of this patent is extended or adjusted under 35 U.S.C. 154(b) by 473 days.

(21) Appl. No.: 18/073,429

(22) Filed: Dec. 1, 2022

(65) Prior Publication Data
US 2023/0102934 A1    Mar. 30, 2023

Related U.S. Application Data

(63) Continuation of application No. PCT/NL2021/050349, filed on Jun. 1, 2021.

(30) Foreign Application Priority Data

Jun. 4, 2020 (NL) .................................. 2025751

(51) Int. Cl.
| | | |
|---|---|---|
| A47J 31/44 | (2006.01) | |
| A47J 31/46 | (2006.01) | |
| A47J 31/60 | (2006.01) | |
| A61L 2/18 | (2006.01) | |
| B08B 3/08 | (2006.01) | |

(Continued)

(52) U.S. Cl.
CPC ....... *A47J 31/4485* (2013.01); *A47J 31/4489* (2013.01); *A47J 31/461* (2018.08); *A47J 31/60* (2013.01); *A61L 2/18* (2013.01); *B08B 3/08* (2013.01); *C11D 7/265* (2013.01); *A61L 2101/36* (2020.08)

(58) Field of Classification Search
None
See application file for complete search history.

(56) References Cited

U.S. PATENT DOCUMENTS 5,611,262 A * 3/1997 Rizzuto ............... A47J 31/4485
99/290
6,499,389 B1 * 12/2002 Probst ................. A47J 31/4485
99/323.1

(Continued)

FOREIGN PATENT DOCUMENTS

| CN | 107920682 A | * 4/2018 | .......... A47J 31/4489 |
|---|---|---|---|
| DE | 19955195 A1 | 5/2001 | |

(Continued)

*Primary Examiner* — Thor S Campbell
(74) *Attorney, Agent, or Firm* — Peacock Law P.C.; Justin R. Muehlmeyer

(57) ABSTRACT

A coffee machine including a frother with an outlet channel for coffee and milk foam, and supply channels for milk, air, and steam respectively, and a nonreturn valve to prevent a fluid in one of the channels from flowing in an undesirable direction. The coffee machine also includes a clean water supply channel that connects to the milk supply channel with a T-junction distant from the frother. The T-junction further connects to a source channel for the milk.

17 Claims, 2 Drawing Sheets

(51) Int. Cl.
*C11D 7/26* (2006.01)
*A61L 101/36* (2006.01)

(56) References Cited

U.S. PATENT DOCUMENTS

| | | | |
|---|---|---|---|
| 8,770,099 B2 * | 7/2014 | Reyhanloo | A47J 31/60 134/25.4 |
| 10,575,675 B2 * | 3/2020 | Fin | A47J 31/4485 |
| 11,147,412 B2 * | 10/2021 | Kroos | A47J 31/46 |
| 12,161,255 B2 * | 12/2024 | Tibbe | A47J 31/4485 |
| 2008/0163896 A1 | 7/2008 | Ioannone | |
| 2011/0005407 A1 | 1/2011 | Reyhanloo | |
| 2014/0373735 A1 * | 12/2014 | Bruinsma | A47J 31/4489 99/453 |
| 2017/0095111 A1 * | 4/2017 | Riessbeck | A47J 31/4489 |
| 2018/0310752 A1 * | 11/2018 | Wessels | A47J 31/4489 |
| 2022/0296032 A1 * | 9/2022 | Klepzig | A47J 31/4485 |

FOREIGN PATENT DOCUMENTS

| | | | | |
|---|---|---|---|---|
| DE | 102011006483 A1 | 10/2012 | | |
| DE | 102019003171 B3 * | 9/2020 | | A47J 31/4485 |
| EP | 2695558 A1 | 2/2014 | | |
| EP | 2732740 A1 * | 5/2014 | | A47J 31/4485 |
| WO | WO-2021009032 A1 * | 1/2021 | | A47J 31/4485 |
| WO | WO-2021246866 A1 * | 12/2021 | | A47J 31/60 |

* cited by examiner

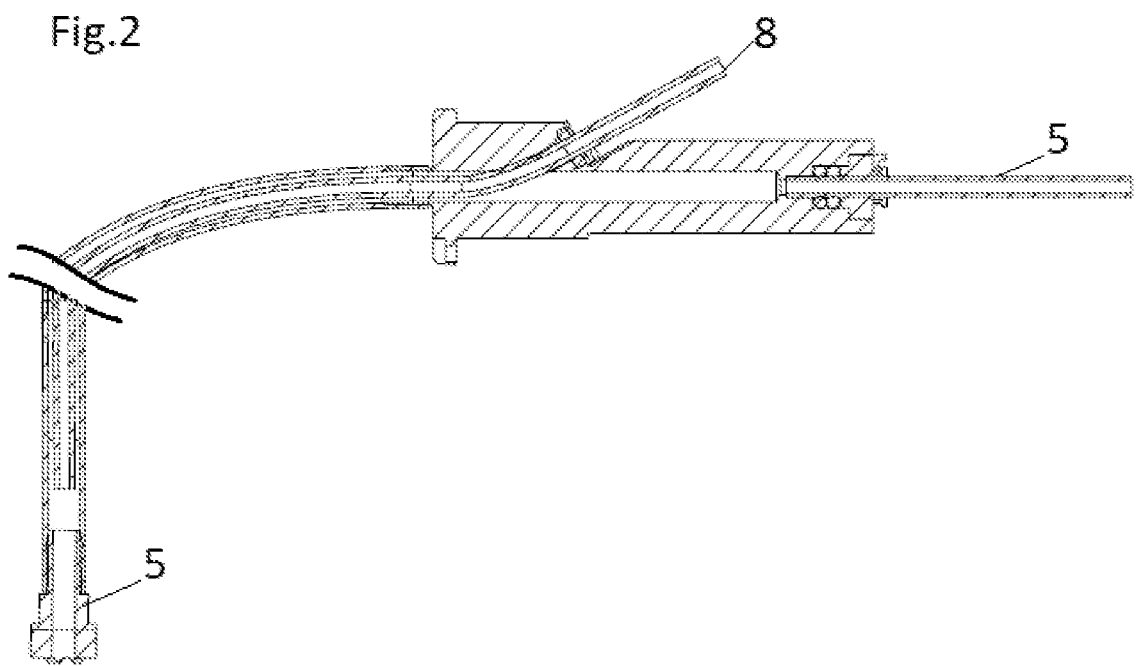

COFFEE OR MILK MACHINE AND METHOD OF OPERATING SUCH A MACHINE

CROSS-REFERENCE TO RELATED APPLICATIONS

This application is a continuation application of International Patent Application No. PCT/NL2021/050349, titled "A Coffee or Milk Machine and a Method of Operating Such a Machine", filed on Jun. 1, 2021, which claims priority to and the benefit of Netherland Patent Application No. 2025751, titled "A Coffee or Milk Machine and a Method of Operating Such a Machine", filed on Jun. 4, 2020, and the specification and claims thereof are incorporated herein by reference.

BACKGROUND OF THE INVENTION

Field of the Invention

The invention relates to a machine comprising a frother with an outlet channel for foamed milk, and supply channels for milk, air, and steam respectively, and provided with a nonreturn valve to prevent a fluid in one of the channels from flowing in an undesirable direction. The invention also relates to a method of operating such a machine. The invention relates to both a coffee machine and a machine to provide foamed milk only.

Background Art

EP 2 695 558 discloses a coffee machine. The nonreturn valve is provided in a supply channel for air that connects to the supply channel for milk, and prevents that milk will flow into the air channel.

When dispensing coffee and foamed milk with such a coffee machine, milk will be sucked into the frother by means of the venturi action that the frother provides. The energy that is required to provide pressure and temperature to the mixture leaving the frother comes from the steam supply, and the air that is supplied to the frother is used to form the foamed milk. This operation is repeated with every serving. Between the servings, the supply channel for the milk is left idle. Consequently, the milk channel fills with air and becomes "dry". Eventually the leftover milk residues in the milk channel will get spoiled. To prevent this spoiling of left-behind milk, frequent cleaning of the milk supply channel is required.

Another drawback of this operation is that when the frother operation starts, the air in the milk supply channel must first leave the milk supply channel. This results in that initially, before the milk foam can start to leave the frother in a stable flow, an irregular sequence of splashing milk droplets leaves the frother and soils the receiving cup.

In addition to soiling the cup, the milk foam bubbles initially have different sizes. When these different size milk foam bubbles are mixed with the subsequent milk foam bubbles with constant bubble size, a so-called disproportionation occurs, i.e. a diffusion of gas from smaller foam bubbles to larger foam bubbles in the milk/air mixture. This leads to even larger foam bubbles and makes the foam unstable. In other words, the foam will disappear quicker than is desirable. This is an important drawback, particularly when the milk foam is used as a top layer on top of coffee since the service life of the milk foam is an important aspect relevant to the catering industry. There is not only the image of the milk foam, i.e. the quality of the served cup of coffee, but also the service life of the milk foam, which sets a limit to the still acceptable delay time at which the cup of coffee with milk foam should be served.

DE-A-10 2011 006 483 discloses a machine with similar problems and deficiencies as described above.

Discussion of the various publications herein is given for more complete background and is not to be construed as an admission that such publications are prior art for patentability determination purposes.

BRIEF SUMMARY OF THE INVENTION

One object of the present invention is to provide a solution for one or more of the above-mentioned problems.

Another object of the invention is to provide a machine which provides a solution to the above problems, yet is still compact as required by market-demand.

Embodiments of the present invention are directed to a machine and a method of operating such a machine in accordance with one or more of the appended claims.

In one embodiment of the present invention, a machine comprising a frother with an outlet channel for milk foam, and supply channels for milk, steam, and air respectively, and provided with a nonreturn valve to prevent a fluid in one of the channels from flowing in an undesirable direction, wherein the machine is further provided with a clean water supply channel that connects to the milk supply channel with a T-junction distant from the frother, wherein the T-junction further connects to a source channel for the milk, wherein the clean water supply channel and the milk supply channel are embodied as a tube in tube construction.

The clean water supply channel serves different purposes, amongst which purposes is that it provides an easy way to introduce water in the milk supply channel after a serving of foamed milk, rather than to leave air inside the milk supply channel in-between separate servings of foamed milk. The presence of water rather than air in the milk supply channel further contributes to the extension of time that the machine may be in operation without intermediate cleaning of the milk supply channel. Further the clean water supply channel can in general also be used to clean the milk supply channel. Even further the clean water supply channel makes possible to avoid the initial sputtering of milk leaving the frother at the start of dispensing milk foam. As mentioned above this initial sputtering undesirably soils the cup. Further the feature that the clean water supply channel and the milk supply channel are embodied as a tube in tube construction makes handling of the respective channels very easy when replacement of a milk supply to which the respective channels lead, is envisaged.

To promote the avoidance of the initial sputtering of milk, it is preferred that the clean water supply channel comprises a control valve connected to a controller which is arranged to cause that during a first stage a burst of clean water is introduced into the milk supply channel immediately before milk enters the milk supply channel coming from the source channel for the milk.

It is further preferred that the T-junction is provided with the nonreturn valve to prevent that clean water from the clean water supply channel enters the source channel for the milk. Preferably the nonreturn valve is of the duckbill type.

The time between the regular cleaning operations of the machine may be further extended by arranging that at least one of the supply channels for the milk and the source channel for the milk are provided with an internal coating with hydrophobic and/or oleophobic properties.

Suitably the coating comprises nanoparticles of silver or silver compounds. And preferably the nanoparticles have a dimension between about $10^{-10}$ and $10^{-7}$ m, preferably in the range of about 1-100 nm, more preferably in the range of about 10-60 nm.

Embodiments of the present invention are also directed to a method of operating a machine, wherein at the start of operating the frother, initially a temporary burst of water supplied by the clean water supply channel is guided in and through the milk supply channel towards the frother.

Preferably the initial temporary burst of water is applied for a duration between about 0.01 and about 3 seconds.

More preferably the initial temporary burst of water is applied for a duration between about 0.05 and about 0.15 seconds.

It is further preferred that after finalizing the operation of the frother, clean water supplied by the clean water supply is guided through the milk supply channel, the frother and the outlet channel.

Beneficially at repeated intervals a container with cleaning agent is placed in fluid communication with the source channel for the milk so as to rinse and clean the machine.

Suitably the cleaning agent is both a descalant to remove limescale and a microbicidal to destroy microbes, such as bacteria.

Preferably the cleaning agent is an acid descalant and microbicidal, comprising about 50-150 ppm peracetic acid.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The invention will hereinafter be further elucidated with reference to a schematic exemplary drawing of a coffee machine according to the invention that is not limiting as to the appended claims. Although the following example relates to a coffee machine, the inventors stress the point that the invention also applies to a machine that exclusively provides foamed milk. This is also logical since the principles of the invention exclusively relate to the foaming of milk and upgrading the quality of the foam, particularly the stability of the foam as explained hereinabove.

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings:

FIG. 2 is an illustration from a cross-sectional view of a coffee machine according to an embodiment of the present invention.

DETAILED DESCRIPTION OF THE INVENTION

Figure 1:
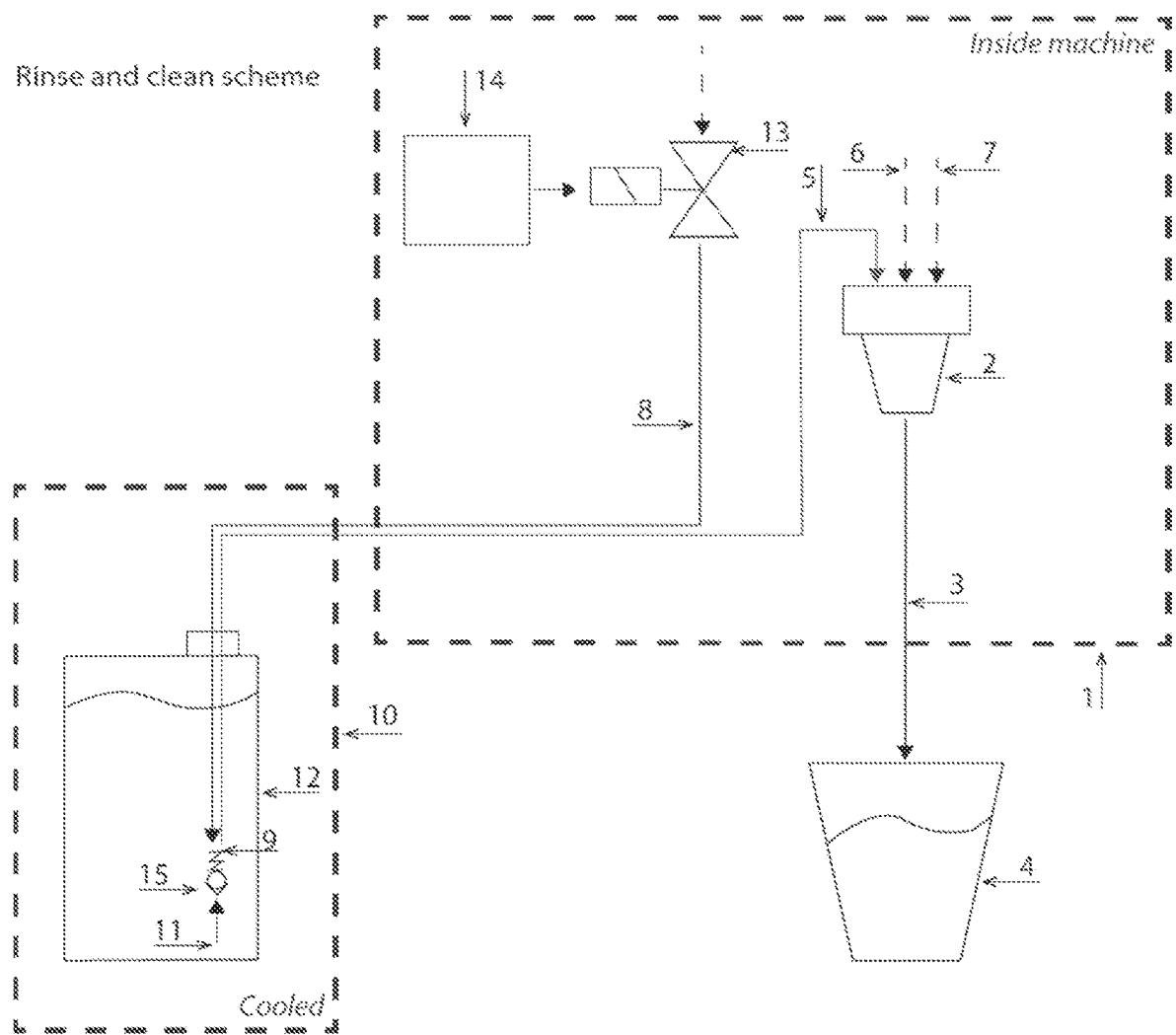
FIG. 1 is a schematic illustration of a method and various features according to an embodiment of the present invention.

The rectangle 1 of dotted lines in FIG. 1 symbolizes a coffee machine according to the invention, which comprises a frother 2 with an outlet channel 3 for coffee and milk foam. The outlet channel 3 provides the coffee and milk foam to a cup underneath the outlet channel 3.

The coffee machine 1 further has a milk supply channel 5, a steam supply channel 6, and an air supply channel 7 connected to the frother 2.

The coffee machine 1 is further provided with a clean water supply channel 8 that connects to the milk supply channel 5 with a T-junction 9 distant from the frother 2. It is noted that the clean water supply channel 8 and the milk supply channel 5 are embodied as a tube in tube construction as shown in FIG. 2. This makes handling of the respective channels 5, 8 very easy when replacement of a milk reservoir 12 to which the respective channels lead, is envisaged.

The T-junction 9 may be provided at any feasible position, both within the limits of the coffee machine 1, or outside the coffee machine 1. The T-junction 9 may be positioned within a cooled environment 10, or outside such a cooled environment 10. The T-junction 9 further connects to a source channel 11 for the milk, which in the shown schematic drawing is placed inside a reservoir 12 for milk which is placed inside a cooled environment 10. This source channel 11 can be very short, for instance 2 mm. It is also feasible that the T-junction is positioned outside the reservoir 12 but preferably inside the cooled environment 10.

Preferably the clean water supply channel 8 comprises a control valve 13 connected to a controller 14 which is arranged to cause that during a first stage of dispensing coffee and milk foam with the frother 2, a burst of clean water is introduced into the milk supply channel 5 immediately before milk enters the milk supply channel 5 coming from the source channel 11 for the milk.

Preferably the T-junction 9 is provided with the nonreturn valve 15 to prevent that clean water from the clean water supply channel 8 enters the source channel 11 for the milk.

Other beneficial features are as follows:
at least one of the milk supply channel 5 and the source channel 11 for the milk are provided with an internal coating with hydrophobic and/or oleophobic properties;
the coating comprises nanoparticles of silver or silver compounds;
the nanoparticles have a dimension between $10^{-10}$ and $10^{-7}$ m, preferably in the range 1-100 nm, more preferably in the range 10-60 nm.

The features of the invention provide the possibility to "jump start" the venturi of the frother 2. This is done by opening the valve 13 for a short period at the start of dispensing coffee and milk foam. This will smoothen the start of the dispense by speeding up the flow towards the frother 2. It will also create a stable start situation by the milk supply channel 5 and frother 2 being filled with water, which results in a more equal dispense of volume and less difference between the first and second cup quality. At the end of any dispensing cycle the valve 13 is opened again to remove the milk from the milk supply channel 5. This prevents the occurrence of spoiled milk in this milk supply channel 5. This end cycle is optional. As an alternative one could also use a "cleanshot" after a certain amount of time. This cleanshot contains a shot of water that removes the milk from the milk supply channel 5, the frother 2 and the outlet channel 3.

Another benefit is that no milk will be stored in uncooled places so as to prevent bacterial growth. In the prior art frequent user actions are required to keep the milk supply channel 5 clean and safe. This is considered user unfriendly and is at all times a hygiene risk. One of the benefits of the invention is that the invention does not need a lot of components, does not require the application of a cool box, and does not have to apply such a cool box as a part inside the coffee machine. On the contrary, the invention provides a solution at low cost while maintaining flexibility of use.

The preferred operation of the coffee machine 1 of the invention is that at the start of dispensing milk by operating the frother 2, initially a temporary burst of water supplied by the clean water supply channel 8 is guided in and through the milk supply channel 5 towards the frother 2. For this purpose valve 13 opens for a short period to initiate the flow of water towards the frother 2. Preferably the initial temporary burst of water is applied for a duration between about 0.01 and about 3 seconds. More preferably the initial temporary burst of water is applied for a duration between about 0.05 and about 0.15 seconds.

Steam is dispensed into a venturi chamber inside the frother 2. This will create under pressure in milk supply channel 5 and will keep the milk flowing towards the frother 2 after closing off the valve 13. The milk originates from the container 12, preferably placed in a cooled environment 10, and arrives in the milk supply channel 5 via the source channel 11 for the milk, which source channel 11 connects with T-junction 9 to the milk supply channel 5. When arriving in the frother 2, the milk will be mixed with air which is also sucked in by the under pressure created by the venturi of the frother 2.

After finalizing the dispensing of coffee by the frother 2, clean water supplied by the clean water supply channel 8 is guided through the milk supply channel 5, the frother 2 and the outlet channel 3. For this purpose, the valve 13 will be opened and water will displace the milk in the milk supply channel 5. The water will not be able to enter the milk reservoir 12 because this is prevented by the non-return valve 15 in the T-junction 9.

It is further preferable that at repeated intervals a container with cleaning agent is placed in fluid communication with the source channel 11 for the milk so as to rinse and clean the coffee machine 1. Suitably the cleaning agent is both a descalant to remove limescale and a microbicidal to destroy microbes, such as bacteria. Preferably the cleaning agent is an acid descalant and microbicidal, comprising about 50-150 ppm peracetic acid.

Although the invention has been discussed in the foregoing with reference to an exemplary embodiment of a coffee machine and a method of its operation, the invention is not restricted to this particular embodiment which can be varied in many ways without departing from the invention. The discussed exemplary embodiment shall therefore not be used to construe the appended claims strictly in accordance therewith. On the contrary the embodiment is merely intended to explain the wording of the appended claims without intent to limit the claims to this exemplary embodiment. The scope of protection of the invention shall therefore be construed in accordance with the appended claims only, wherein a possible ambiguity in the wording of the claims shall be resolved using this exemplary embodiment.

Embodiments of the present invention can include every combination of features that are disclosed herein independently from each other. Although the invention has been described in detail with particular reference to the disclosed embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference. Unless specifically stated as being "essential" above, none of the various components or the interrelationship thereof are essential to the operation of the invention. Rather, desirable results can be achieved by substituting various components and/or reconfiguration of their relationships with one another.

Note that in the specification and claims, "about" or "approximately" means within twenty percent (20%) of the numerical amount cited.

What is claimed is:

1. A machine comprising:
   a frother comprising an outlet channel for milk foam, and supply channels for milk, steam, and air respectively, and comprising a nonreturn valve to prevent a fluid in one of the channels from flowing in an undesirable direction;
   a clean water supply channel that connects to the milk supply channel with a T-junction distant from the frother, wherein the T-junction further connects to a source channel for the milk, and wherein the clean water supply channel and the milk supply channel comprise a tube in tube construction.

2. The machine of claim 1, wherein the clean water supply channel comprises a control valve connected to a controller which is arranged to cause that a burst of clean water is introduced into the milk supply channel immediately before milk enters the milk supply channel coming from the source channel for the milk.

3. The machine of claim 1, wherein the T-junction comprises the nonreturn valve to prevent that clean water from the clean water supply channel enters the source channel for the milk.

4. The machine of claim 3, wherein the nonreturn valve is of the duckbill type.

5. The machine of claim 1, wherein at least one of the milk supply channel and the source channel for the milk is provided with an internal coating with hydrophobic and/or oleophobic properties.

6. The machine of claim 5, wherein the coating comprises nanoparticles of silver or silver compounds.

7. The machine of claim 6, wherein the nanoparticles have a dimension between about $10^{-10}$ and about $10^{-7}$ m.

8. The machine according to claim 1, wherein the machine is a coffee machine.

9. A method of operating a machine according to claim 1, comprising the step of, at the start of operating the frother, initially bursting a temporary burst of water supplied by the clean water supply channel guided in and through the milk supply channel towards the frother.

10. The method according to claim 9, wherein the initial temporary burst of water is applied for a duration of between about 0.01 and about 3 seconds.

11. The method according to claim 10, wherein the initial temporary burst of water is applied for a duration of between about 0.05 and about 0.15 seconds.

12. The method according to claim 9, further comprising the step of, after operating the frother, guiding clean water through the milk supply channel, the frother and the outlet channel, wherein the clean water is supplied by the clean water supply channel.

13. The method according to claim 9, further comprising the step of placing a container with cleaning agent in fluid communication with the source channel for the milk, at repeated intervals, so as to rinse and clean the machine.

14. The method according to claim 13, wherein the cleaning agent is both a descalant to remove limescale and a microbicidal to destroy microbes.

15. The method according to claim 13, wherein the cleaning agent is an acid descalant and microbicidal, comprising about 50-150 ppm peracetic acid.

16. The machine of claim 6, wherein the nanoparticles have a dimension in the range of about 1-100 nm.

17. The machine of claim 6, wherein the nanoparticles have a dimension in the range of about 10-60 nm.

* * * * *